United States Patent
Chou

(10) Patent No.: US 8,029,806 B2
(45) Date of Patent: Oct. 4, 2011

(54) METHOD FOR DIAGNOSING OF MYCOBACTERIUM TUBERCULOSIS

(75) Inventor: George Chin Sheng Chou, Tainan County (TW)

(73) Assignee: AsiaGen Corporation, Tainan County (TW)

( * ) Notice: Subject to any disclaimer, the term of this patent is extended or adjusted under 35 U.S.C. 154(b) by 584 days.

(21) Appl. No.: 12/104,211

(22) Filed: Apr. 16, 2008

(65) Prior Publication Data
US 2009/0263793 A1    Oct. 22, 2009

(51) Int. Cl.
*A61K 39/04*    (2006.01)
*A61K 39/02*    (2006.01)
*C07H 21/04*    (2006.01)

(52) U.S. Cl. ............... 424/248.1; 424/185.1; 424/234.1; 435/4; 435/6; 536/23.1; 536/24.32; 536/24.33

(58) Field of Classification Search ............... 424/185.1, 424/234.1, 248.1; 435/4, 6; 536/23.1, 24.32, 536/24.33
See application file for complete search history.

(56) References Cited

FOREIGN PATENT DOCUMENTS
WO    2007034118 A1    3/2007

OTHER PUBLICATIONS

Bergey's Manual of Systematic Bacteriology, vol. 2, pp. 1452-1457, Sneath et al, eds., Williams & Wilkins, Baltimore, MD 1984.*

* cited by examiner

*Primary Examiner* — Rodney P. Swartz
(74) *Attorney, Agent, or Firm* — WPAT, P.C.; Anthony King

(57) ABSTRACT

The present invention relates to a method and a kit for detecting *Mycobacterium tuberculosis* (MTB) or Nontuberculous mycobacteria (NTM) of patients. The present invention also relates to primers and probes used to detect *Mycobacterium tuberculosis* (MTB) or Nontuberculous mycobacteria (NTM) by performing PCR.

5 Claims, 5 Drawing Sheets

FIGURES

*M. kansasii* clinical samples

TB and MK clinical samples

METHOD FOR DIAGNOSING OF MYCOBACTERIUM TUBERCULOSIS

FIELD OF THE INVENTION

The present invention relates to a method and a kit for detecting *Mycobacterium tuberculosis* (*M. tuberculosis*) and Nontuberculous mycobacteria (NTM) in a sample by the usage of a nested polymerase chain reaction (PCR). The present invention also relates to primers and probes for detecting the presence of *M. tuberculosis* and Nontuberculous mycobacteria.

BACKGROUND OF THE INVENTION

*Mycobacterium tuberculosis* (MTB) is a member of *mycobacterium* among gram-positive bacteria. Nontuberculous mycobacterium (NTM) is an atypical *mycobacterium*. "Mycobacterium other than tuberculosis" is a generally called for mycobacteria except *M. tuberculosis*. An example is *Mycobacterium avium* complex that has attracted huge attention since it was extensively isolated from specimens of AIDS patients.

Tuberculosis (TB) is the leading infectious killer of youths and adults and the first and most infectious disease worldwide. One third of the population in the world is currently infected and 20 million of those infected population are active cases. TB will kill 30 million people in this decade. More than 50 million people may already be infected by multidrug-resistant (MDR) strains of TB. TB is now becoming the leading cause of death among HIV positive people and it has a rapid fatality of 80%.

Tuberculosis is caused by infecting with *M. tuberculosis*, a bacillus bacterium. It is spread by aerosol droplets and causes irreversible lung destruction. If it escapes from the lung, it may cause systemic disease affecting many organs including bone, joint, liver, spleen, gastrointestinal tract and brain. 50% of people exposed to *M. tuberculosis* are infected by the bacterium and 15% of those infected people develop into a disease. Poverty, malnutrition and overpopulation contribute dramatically to the perseverance and wild spread of tuberculosis.

In the past, means of controlling TB have involved the use of combinations of antibiotics. Recently, because of complications caused by MDR strains, the number and combination of antibiotics administered must be individually tailored according to the strain. In extreme cases, surgical removal of the infected portion of the lung is required.

Traditionally, the diagnosis of TB has been made on the basis of clinical findings and chest radiographs and confirmed by sputum or tissue smears that show TB bacilli. These methods remain the "gold standard" for diagnosis.

Nontuberculous mycobacteria (NTM) are ubiquitous in the environment and include more than 90 different species, causing colonization, infection, and pseudo-outbreaks in health care settings. Data suggest that the frequency of nosocomial outbreaks due to NTM may be increasing, and reduced hot water temperatures may be partly responsible for this phenomenon. Attention to adequate high-level disinfection of medical devices and the use of sterile reagents and biologics will prevent most outbreaks. Because NTM cannot be eliminated from the hospital environment and they present an ongoing potential of infection, NTM should be considered in all cases of nosocomial infection, and careful surveillance must be used to identify potential outbreaks. Analyses of the species of NTM and the specimen source may assist to determine the significance of a cluster of isolated samples. Once an outbreak or pseudo-outbreak is suspected, molecular techniques should be applied promptly to determine the source and identify appropriate control measures.

Evidence suggests that nosocomial transmission of these organisms is increasing, and results in conditions ranging from harmless colonization to invasive infection. NTM may also contaminate microbiological specimens, which leads to unnecessary therapy and potentially harmful diagnostic procedures.

NTM have been classified into 4 groups by colony growing rate and the color showed after those colonies are illuminated:

Group 1: slow-growing photochromogens. Their colonies turn to yellow after being illuminated, including *Mycobacterium kansasii*, *Mycobacterium marinum*, *Mycobacterium simiae* and *Mycobacterium asiaticum*, which are all pathogenic bacteria. The most prevalent one among these is *Mycobacterium kansasii*.

Group 2: slow-growing scotochromogens. Their colonies turn to yellow without being illuminated, including *Mycobacterium scrofulaceum*, *Mycobacterium xenopi*, *Mycobacterium szulgai* and *Mycobacterium flavescens*, which are all pathogenic bacteria, and *Mycobacterium gordonae*, which is a non-pathogenic bacterium. The most prevalent one among these is *Mycobacterium scrofulaceum*.

Group 3: Slow-growing nonchromogens. Their colonies' colors are steady even after those colonies are illuminated, including *Mycobacterium avium* complex, *Mycobacterium malmoense*, *Mycobacterium shimoidei* and *Mycobacterium flavescens*, which are all pathogenic bacteria, and *Mycobacterium gastri*, *Mycobacterium terrae* and *Mycobacterium triviale*, which are non-pathogenic bacteria. The most prevalent one among these is *Mycobacterium avium* complex.

Group 4: Rapidly growing mycobacteria. They include *Mycobacterium fortuitum*, *Mycobacterium chelonae-abscessus* and *Mycobacterium chelonae-chelonae*, which are all pathogenic bacteria, and *Mycobacterium phlei*, *Mycobacterium smegmatis*, *Mycobacterium vaccae* and *Mycobacterium flavescens*, which are non-pathogenic bacteria.

Recently, investigation of putative nosocomial outbreaks of MTB or NTM has been aided by the use of molecular techniques to identify the source and mode of transmission. The development of DNA probes, polymerase chain reaction (PCR) assays, and liquid media now allow more sensitive and rapid diagnoses for MTB and NTM.

Unfortunately, increased sensitivity of rapid techniques is not always associated with increased specificity. For example, known method (such as real-time PCR assay) using the LightCycler (LC) instrument provides a rapid, sensitive and specific means to identify *M. tuberculosis*. PCT patent application No.: WO2007034118 disclosed a method for detecting the possible presence of bacteria belonging to the Mycobacterium tuberculosis complex in a biological sample, using real time PCR technique and comprising a step of amplifying with a pair of PCR primers and a pair of FRET probes the hsp 65 gene and detecting the emitted fluorescence. However, the use of LC as a routine diagnosis of *M. tuberculosis* remains limited at present. It is because the installment and maintenance cost are too expensive to be afforded by most of the users in the medical centers.

There is another method for detecting *M. tuberculosis*. Korean patent application KR20030075315 disclosed a method for simultaneous detection of tubercle bacillus (TB) and Nontuberculous mycobacteria (NTM) by multiple-nested polymerase chain reaction, thereby rapidly detecting tubercle bacillus and nontuberculous mycobacteria. Nested PCR is often more successful in specifically amplifying long DNA fragments than conventional PCR, but it requires more detailed knowledge of the target sequences.

SUMMARY OF THE INVENTION

The present invention provides a kit for detecting the presence or absence of *Mycobacterium tuberculosis* and Nontuberculous mycobacteria in a sample using a nested polymerase chain reaction.

The present invention also provides a method for detecting the presence or absence of *Mycobacterium tuberculosis* and Nontuberculous mycobacteria in a sample using a nested polymerase chain reaction.

The present invention further provides novel nucleotide sequences for detecting the presence or absence of *Mycobacterium tuberculosis* and Nontuberculous mycobacteria.

DETAILED DESCRIPTION OF THE INVENTION

Figure 1:
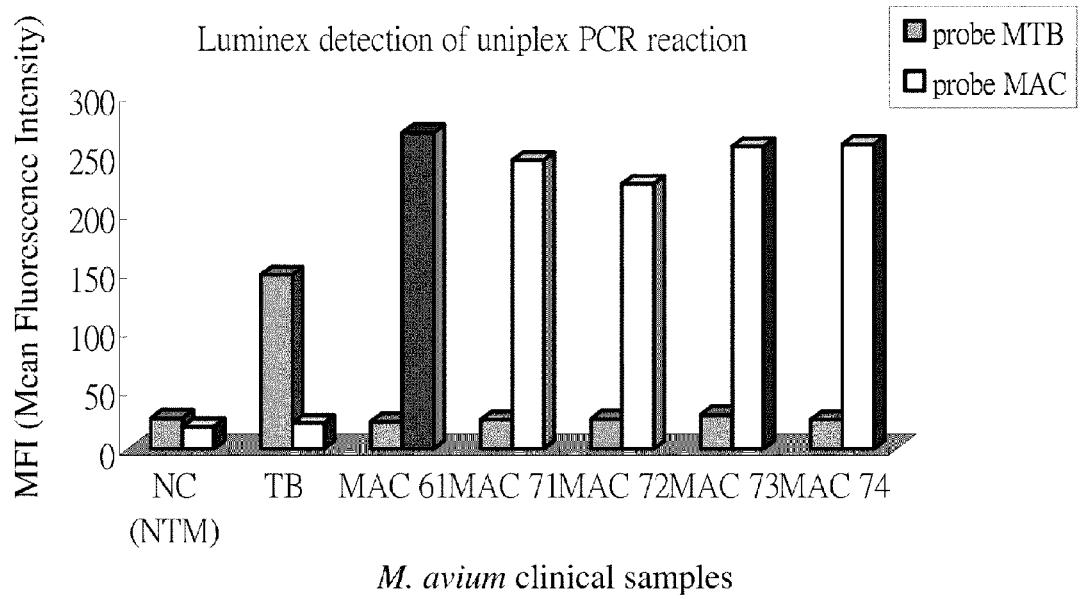
FIG. 1 illustrates the result of a PCR product by uniplex PCR reaction hybridized with MTB probe and MAC probe, then assayed by Luminex TB represents a specimen from a tuberculosis patient. MAC61, MAC71, MAC72, MAC73 and MAC74 represent specimens from *Mycobacterium avium* complex patients. NC (NTM) represents the negative control (Nontuberculous mycobacteria).

The present invention provides a method incorporating a uniplex, duplex or multiplex PCR assay and a subsequent uniplex, duplex or multiplex liquid is hybridized by MTB and/or NTM oligonucleotide probes conjugated with fluorescent beads to rapidly screen infectious samples of MTB and/or NTM. Highly valid and species-specific primer sets are used to simultaneously or separately amplify multiple diagnostic regions unique to each individual pathogen strain such as *Mycobacterium tuberculosis* (MTB), Mycobacterium avium complex (MAC), *Mycobacterium kansasii* (MK) and Rapidly growing mycobacteria (RGM).

The present invention relates to primers and probes for rpoB gene of MTB and NTM. After isolating samples from pathogen strains described above, fragments are amplified by uniplex, duplex or multiplex PCR in one reaction tube by one primer pair or a plurality of primer pairs designed for MTB and/or NTM. Subsequently, PCR products are further hybridized with probes to identify the bacteria in the Luminex detection system. The procedure is to detect the presence of MTB and/or NTM in PCR products by oligonucleotide probes conjugated with fluorescent beads which can recognize nucleotide sequences within PCR products, and oligonucleotide probes conjugated with fluorescent beads are used to differentiate MTB and NTM.

PCR technology can amplify a large amount of bacterial DNA from a small amount with easy manipulation, therefore, the PCR technology is suitable for identifying slow-growing bacteria. Recent years, some researches on MTB identification by PCR focused on 16S rRNA, 23S rRNA, rpoB gene or a sandwich region inside the 16S-23S rRNA intergenic region. Each of those targets, include 16S rRNA, 23S rRNA, rpoB gene and a sandwich region inside the 16S-23S rRNA intergenic region, has a highly conserved region located on both ends of its sequence among various MTB strains. However, each of those targets has a polymorphic or variable region located on the middle site of its sequence among various MTB strains. These regions are amplified by PCR and then cleaved by some restriction enzymes for identification. Various bacteria are compared and identified by PCR such as PCR restriction fragment length polymorphism (PCR-RFLP) or nested PCR. PCR-RFLP not only can be used to identify various NTM, but also judge if there are rifampin resistance NTM. The present invention indicates that PCR products can be further used to determine bacteria strain having rifampin resistance by restriction enzyme involved assay such as PCR-RFLP or PCR-SNP.

Resolution of the mixed and amplified PCR products is achieved by PCR products hybridized to correspondent probe sequences, which are attached to unique sets of fluorescent beads.

The hybridized beads are processed through a liquid phase reaction, which detect the presence of each PCR product. The method herewith is optimized to allow maximum sensitivity in a multiplex format.

A high-efficient demonstration is performed where 10 simulated and clinical samples are spiked with different pathogen DNA. The samples are processed to extract DNA and subjected to multiplex PCR-liquid bead detection. The assay correctly identifies the presence or absence of each pathogen.

These pathogens include *Mycobacterium tuberculosis* (MTB) and Nontuberculous mycobacteria (NTM). NTM also consist of photochromogens, scotochromogens and nonchromogens according to Runyon group classification. Further, NTM includes *Mycobacterium avium complex* (MAC), *Mycobacterium kansasii* (MK) and Rapidly growing mycobacteria (RGM) herein.

Uniplex, duplex and multiplex PCR are used for deciding effects of each primer pair of those pathogens, and results show individual effects of each primer pair for differentiating MTB and NTM. There is no crossing interference between primer pairs of MTB and NTM.

Methodology of the Analysis Procedures of Luminex

The methodology is based on the principle that fluorescent microspheres with unique fluorescent profiles, called classifications, can be cross-linked to different and analyte-specific reagents and used to create a fluorescence-based array capable of simultaneously assaying multiple analytes in each sample (Robert et al., Clinical Chemistry. 46:996-998, 2000). The bead classifications are obtained separately from the Luminex Corporation with surface carboxyl groups for chemical cross-linking to different analyte-specific reagents, which in our invention are 5'-amino-modified oligodeoxynucleotides. Each bead classification has a unique spectral address based on its 658 nm/712 nm emission ratio when excited by the 635 nm laser in the Luminex$^{100}$ instrument. The Luminex software uses this spectral profile to assign beads to their classifications, and each classification occupies a known position on a dot plot of 658 nm vs 712 nm fluorescence. Thus, multiple bead classifications can be combined in one sample, and the Luminex software processes the fluorescent signals to generate an array of bead classifications on the dot plot of 658 nm/712 nm fluorescence. Determination of the amounts of the different analytes bound to each bead classification is accomplished by coincident excitation of the beads with the 532 nm laser in the Luminex$^{100}$ instrument. Thus, labeling bead-bound analytes with a fluorescent reporter molecule such as phycoerythrin, which emits at 575 nm when excited at 532 nm, produces a third fluorescent signal which allows the amounts of analytes bound to the beads to be quantified. Thus, in each sample, the amounts of multiple analytes can be determined from the emissions of a single fluorescent reporter molecule because the analyte specificity and position of each bead classification in the array is known.

Term Definition

The following definitions are provided to facilitate understanding of certain terms used throughout this specification.

Nucleic Acid

As used herein, "nucleic acid" is meant a sequence of two or more covalently bonded naturally occurring or modified deoxyribonucleotides or ribonucleotides.

Reporter

As used herein, "reporter" is meant a chemical group or moiety that is capable of being detected by a suitable detection system, particular in the context of detecting molecules containing the detection group after or during molecular separation. Examples of the reporter include various enzymes, fluorescent materials, luminescent materials, bioluminescent materials, radioactive materials, positron emitting metals using various positron emission tomographies, and nonradioactive paramagnetic metal ions.

Examples of above mentioned enzymes include horseradish peroxidase, alkaline phosphatase, beta-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes colored microspheres (CMS); luminol; examples of bioluminescent materials include luciferase, luciferin, and aequorin; and examples of suitable radioactive material include 125I, 131I, 111In or 99Tc.

The reporter may be coupled or conjugated either directly, or indirectly through an intermediate using technique known in the prior art, for example, U.S. Pat. No. 4,741,900 for metal ions which can be conjugated to antibodies for using as diagnostics according to the present invention, to a binder used through the present invention for specific target recognition. In correspondence to different form of target (nucleic acid or antigen), the binder may be a fragment of nucleic acid (e.g. a PCR primer), or an antibody (or fragment thereof).

Recognize Particle

As used herein, "recognize particle" is meant a molecule or a group of molecules capable of binding, conjugating or absorbing to a ligand by chemical or physical force, to facilitate a subsequent separation in any suitable separation techniques used in the present invention. Representative examples of such molecules include recombinant proteins, glycoproteins, glycosaminoglycans, proteoglycans, integrins, enzymes, lectins, selectin, cell-adhesion molecules, toxins, bacterial pili, transport proteins, receptors involved in signal transduction or hormone-binding, hormones, antibodies, major histocompatability complexes, immunoglobulin superfamilies, cadherins, DNA or DNA fragments, RNA or RNA fragments, whole cells, cell fragments, tissues, bacteria, fungi, viruses, parasites, prions, synthetic analogs or derivatives thereof. Particles include magnetic beads, microspheres; and the like.

One particular useful example of the separator is carboxylate microspheres, since they have been used for many years in radioimmunoassays, ELISAs, and cell separation assays. These beads are synthesized by dispersing ferrite crystals in a suspension of styrene/divinylbenzene monomers and polymerizing this cocktail into microspheres. Molecular biology applications, especially PCR, require further that the microspheres be encapsulated to ensure that no iron, which can interfere with polymerases and other enzymes, remains on the surface of the bead or escapes into solution. Available surface modifications on polystyrene based magnetic beads include both carboxylic acid (—vCOOH) and primary amines (—NH2). All commercial magnetic microspheres are actually super paramagnetic, that is, they exhibit no magnetic remanence or hysteresis. Magnetic oligo-dT beads have been in routine use in molecular biology to purify mRNA for many years.

Target Gene

The present invention is related to nucleotide sequences comprising highly specific oligonucleotide primers that are synthesized from and hybridized to specific portions of the rpoB gene of *M. tuberculosis* and Nontuberculous mycobacteria having the nucleotide sequence set forth in SEQ ID NOs: 1-4.

In addition, the present invention also provides novel probes in SEQ ID NOs: 5-8 for identifying the nested PCR products. Therefore, the present invention provides nucleotide sequences for detecting the presence or absence of *M. tuberculosis* or Nontuberculous mycobacteria.

These single-stranded primers are comprised of nucleotide sequences including naturally occurring nucleotides and any variants thereof. By "naturally occurring nucleotides" is intended adenosine triphosphate, guanosine triphosphate, cytosine triphosphate, thymidine triphosphate, uridine triphosphate, and inosine triphosphate. By "any variants thereof" is intended any nucleotides comprising modified bases of the form N6-(6-aminohexyl) (as in N6-(6-aminohexyl) dATP or N6-(6-aminohexyl) ATP), or comprising bases modified as 5'-thiol, 5'-phospho, 5'-methyl, 5'-biotinylated, 5'-amino, or 5'-fluoro (as in 5'-fluoro-deoxyadenosine).

These primers are designed for desirable characteristics, including inability to form hairpin loops. Additionally, when any two of these primers are used as a primer pair for a polymerase chain reaction method according to the present invention, they do not hybridize to each other. All of these characteristics enable a highly sensitive, highly specific nested polymerase chain reaction approach for detection of the *M. tuberculosis* or Nontuberculous mycobacteria in potentially infected samples.

Primers for Multiplexed PCR

In an embodiment of the present invention, these primers are used in a nested polymerase chain reaction (PCR) method to detect the presence of the *M. tuberculosis* rpoB gene in a purified sample nucleic acid mixture, the nucleotide sequences of which have been extracted from a potentially infected sample. By "nested PCR" method is intended a two-staged polymerase chain reaction process. In a first-stage polymerase chain reaction, a pair of "outer" oligonucleotide primers, consisting of an upper and a lower primer that flank a particular "first target" nucleotide sequence in the 5' and 3' position, respectively, are used to amplify that first sequence. In a second-stage polymerase chain reaction, a second set of "inner" or "nested" oligonucleotide primers, also consisting of an upper and a lower primer, is used to amplify a smaller "second target" nucleotide sequence that is contained within the first target nucleotide sequence.

The upper and lower inner primers flank the second target nucleotide sequence in the 5' and 3' positions, respectively. By "flanking primers", intended primers that are complementary to segment on the 3'-end portions of the double-stranded target nucleotide sequence that is amplified during the PCR process. By "target" nucleotide sequence is intended a nucleotide sequence comprising a predetermined portion of the *M. tuberculosis* rpoB gene set forth in SEQ ID NOs: 1 and 2.

Samples of *M. Tuberculosis*

The primers and nested PCR method of the present invention can be utilized for the detection of the presence or absence of the *M. tuberculosis* or Nontuberculous mycobacteria in any sample nucleic acid mixture isolated from any tissue sample suspected of harboring the *M. tuberculosis* or Nontuberculous mycobacteria. By "sample nucleic acid mixture" is intended a sample containing nucleic acids and mixtures thereof from any individual, strain, species, or genera of organism.

Procedures of PCR—Isolate DNA

The nested PCR method of the present invention comprises the following steps. A sample nucleic acid mixture is first isolated from a tissue sample suspected of being infected with the *M. tuberculosis* or Nontuberculous mycobacteria and then purified by centrifugation. Methods for isolation and preparation of the purified *M. tuberculosis* nucleic acid mixture are available in the art. See examples, Yuen K Y, et al., J Clin Microbiol. 1997 35(6):1385-9; Yam W C, et al. Diagn Microbiol Infect Dis. 2004 48(4):271-5.

Analyze Product of PCR

The amplification products of the first- and second-stage polymerase chain reaction may be analyzed to identify the presence or absence of the first and second targeted nucleotide sequences comprising specific portions of the rpoB gene. Identification of the amplification products, as being derived from the *M. tuberculosis* rpoB gene, could be accomplished by any one of several methods known in the art to detect amplified nucleotide sequences. These methods include, but are not limited to, determination of size, restriction enzyme digestion pattern, subsequent cloning of amplification products, Southern blot hybridization, with an oligonucleotide probe internal to the nucleotide sequence being amplified, or DNA sequencing.

Analyze Product of PCR—Labeled Primers

In another embodiment, labeled primer pairs in the first or/and second stage of amplification could be used in the nested PCR amplification to detect the amplification product directly. Commonly employed labels include, but are not limited to, fluorescent molecules, radioactive molecules, chromogenic substrates, biotin, acridinium ester and acridinium-9-carboxamide. The methods for biotinylating nucleic acids are well known in the art, as are methods for introducing fluorescent molecules and radioactive molecules into oligonucleotides and nucleotides. In the preferred embodiment of the invention, the inner pair of oligonucleotide primers is labeled by biotin.

When biotin is employed, it is detected by avidin, streptavidin or the like, which is conjugated to a detectable marker, such as an enzyme (e.g., horseradish peroxidase). Enzyme conjugates are commercially available from, for example, Vector Laboratories (Burlingame, Calif.). Steptavidin binds with high affinity to biotin, unbound streptavidin is washed away, and the presence of horseradish peroxidase enzyme is then detected using a luminescence-emission substrate in the presence of peroxide and appropriate buffers. The product may be detected using a Berthold Luminometer (Pforzheim, Germany).

Detection methods are well known for fluorescent, radioactive, chemiluminescent, chromogenic labels, as well as other commonly used labels. Briefly, chemiluminescence can be identified and quantitated most directly by their emission wavelengths and intensity.

Analyze Product of PCR—Luminex

Kits of Invention

The present invention provides a kit for detecting the presence or absence of *Mycobacterium tuberculosis* and Nontuberculous mycobacteria in a sample using a nested polymerase chain reaction, comprising primer pairs set forth in SEQ ID NOs: 1 to 4.

The kit of the present invention could be applied to currently established PCR methods (such as one-tube or two-tube nested PCR). In the preferred embodiment, the kit of the present invention is applied to one-tube nested PCR reaction.

The present invention provides for "kits" comprising the elements necessary to detect the presence or absence of the *M. tuberculosis* or Nontuberculous mycobacteria in a sample using the nested PCR method of the invention. Such a kit may comprise a carrier being compartmentalized to receive in close confinement therein one or more container means, such as tubes or vials.

One or more said container means of such a kit may contain one or more enzymes or reagents to be used in the nested PCR method of the invention. These enzymes may be present singly or in a mixture, in the lyophilized state or in an appropriate storage buffer. The kit may also contain any additional materials needed to carry out the detection method of the invention, such as buffers, extraction and purification reagents, nucleic acids, nucleotides (dNTPs), pipettes, plates, filter paper, gel electrophoresis materials, transfer materials, and the like.

The kit of the invention further comprises a probe to detect the amplification product of the nested PCR. In the preferred embodiment of the invention, the probes are SEQ ID NOs. 5 to 8.

The probe can specifically recognize a particular target. Commonly employed labels include, but are not limited to, biotin, fluorescent molecules, radioactive molecules, chromogenic substrates, chemi-luminescence, and the like. Detection methods are well known for fluorescent, radioactive, chemiluminescent, chromogenic labels, as well as other commonly used labels.

The following experiments are offered by way of illustration and not by way of limitation.

EXAMPLES

The examples below are non-limiting and are merely representative of various aspects and features of the present invention.

Materials and Purifying DNA from Patient Specimens
1. Primer pairs and probes
    (1) Tbc1and TbcR5—MTB primer pair (SEQ. ID. NOs. 1 and 2)
    (2) NTM-M5 and NTM-RM3—NTM primer pair (SEQ. ID. NOs. 3 and 4)
    (3) MTB probe—*Mycobacterium tuberculosis* (SEQ. ID. NO. 5)
    (4) probe for *Mycobacterium avium* complex—MAC (SEQ. ID. NO. 6)
    (5) probe for *Mycobacterium kansasii*—MK (SEQ. ID. NO. 7)
    (6) probe for Rapidly growing mycobacteria—RGM (SEQ. ID. NO. 8)
2. Clinical Specimens:
    (1) *Mycobacterium tuberculosis* (MTB)
    (2) *Mycobacterium avium* (MAC)
    (3) *Mycobacterium kansasii* (MK)
    (4) Rapidly growing mycobacteria (RGM)
1. Added 1 ml 1×PBS into eppendorf microtube, scrapped colony by loop and mixed well with PBS then vortexed and heated for 30 min at 80-90° C.
2. Stood still until cooled down to room temperature, centrifuged 1000×g for 5 min Discarded supernatant and added 400 µl TE buffer (Tris 10 mM, pH 8.0, EDTA 1 mM) and 50 ml lysozyme (10 mg/ml). Vortexed for a while followed by put in water bath at 37° C. for an hour.
3. Took out samples and added 70 ml 10% SDS and 6 ml proteinase K (10 mg/ml). Vortexed for a while then put in water bath at 60° C. for 10 min
4. Took out sample and added 100 ml 5 M NaCl, inverted several times, and added 80 µl CTAB (cetyltrimethyl ammonium bromide)/NaCl, inverted several times. Put in water bath at 65° C. for 10 min
5. Added into equal volume chloroform/isoamyl alcohol (24:1) and inverted several times, centrifuged 10000×g for 5 min then transferred supernatant to a new eppendorf microtube.
6. Added 500 µl isopropanol and put in a refrigerator at −20° C. for 30 min. Centrifuged 14000×g for 20 min and discarded supernatant.
7. Added 500 ml ice 70% alcohol and centrifuged 14000×g for 5 min Discarded supernatant and dried out then added 50 µl sterile water.

PCR Reaction
    (1) Components in 0.2 ml PCR tube:

| Reagent | Volume |
| --- | --- |
| DNA | 1 µl (3 ng/µl) |
| Reaction mixture | 49 µl |
| **wherein reaction mixture contains | |
| 10x PCR polymerase buffer | 5 µl |
| Primer Tbc1 (10 µM) | 1 µl |
| Primer TbcR5 (10 µM) | 1 µl (biotin label) |
| Primer NTM-M5 (10 µM) | 1 µl (biotin label) |
| Primer NTM-RM3 (10 µM) | 1 µl |
| dNTP (2.5 mM) | 2.5 µl |
| Taq DNA polymerase (2 U/µl) | 0.25 µl |
| ddH$_2$O | 37.25 µl |

(2) After adding material mentioned above and mixed well, began the PCR amplification procedure with the program described in Table 1:

TABLE 1

| | Temperature | Time | Number of cycles |
| --- | --- | --- | --- |
| 1 | 95° C. | 5 min | 1 cycle |
| 2 | 95° C. | 30 sec | 30 cycles |
| | 65° C. | 30 sec | |
| | 72° C. | 60 sec | |
| 3 | 72° C. | 5 min | 1 cycle |
| 4 | 4° C. | Hold | — |

Hybridization and Detective Reaction

1. Took 5 µl PCR product and mixed well with 10 µl ddH$_2$O, reacted at 95° C. for 10 min.
2. Added 1 µl MTB microsphere probe and MAC microsphere probe or MK microsphere probe or RGM microsphere probe, respectively. 33 µl 1.5×TMAC (4.5 M teramethtlammonium chloride, 0.15% SDS, 75 mM pH 8.0 Tris-HCl, 6 mM pH 8.0 EDTA) were also added.
3. After mixed well, reacted at 46° C. for an hour.
4. Reactant that completed hybridization centrifuged at 14000 rpm for 2 min, removed supernatant.
5. Rinsed with 50 nl 1×TMAC (3 M teramethtlammonium chloride, 0.15% SDS, 50 mM pH 8.0 Tris-HCl, 4 mM pH 8.0 EDTA), centrifuged 14000 rpm for 2 min and got rid of the supernatant.
6. Repeated step 5.
7. Diluted 1 mg/ml streptavidin-phycoerythrin (SA-PE, 1:250) with 1×TMAC and mixed well with 50 µl sample. Shaking avoided light and present color for 10 min
8. Poured into 96-well dish with samples then went on Luminex assay.

Figure 2:
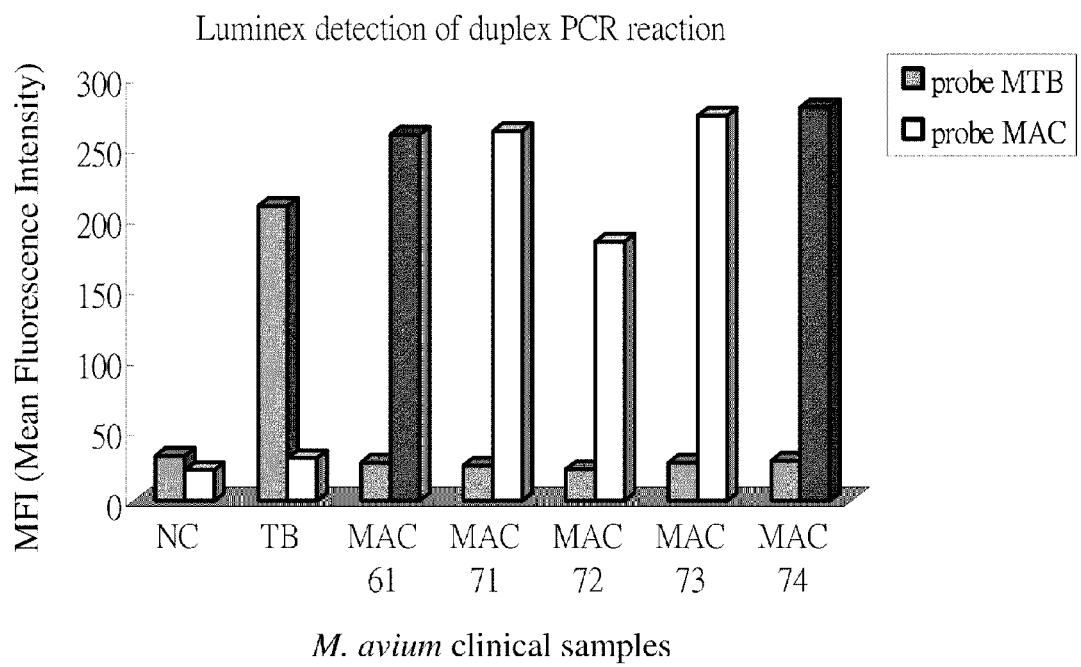
FIG. 2 illustrates the result of PCR products by duplex PCR reaction hybridized with MTB probe and MAC probe, then assayed by Luminex TB represents a specimen from a tuberculosis patient. MAC61, MAC71, MAC72, MAC73 and MAC74 represent specimens from *Mycobacterium avium* complex patients. NC represents the negative control.
Figure 3:
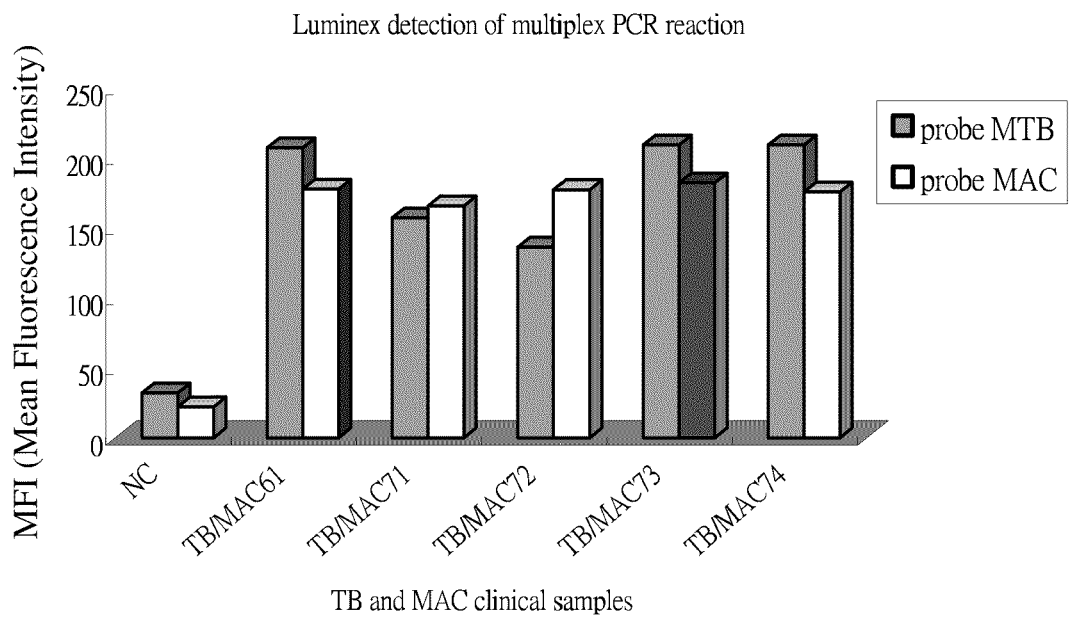
FIG. 3 illustrates the result of PCR products by multiplex PCR reaction hybridized with MTB probe and MAC probe, then assayed by Luminex TB represents a specimen from a tuberculosis patient. MAC61, MAC71, MAC72, MAC73 and MAC74 represent specimens from *Mycobacterium avium* complex patients. "TB/MAC" represents specimens containing a specimen from the tuberculosis patient and a specimen from one of the *Mycobacterium avium* complex patients. NC represents the negative control.

Result 1. 10 patient specimens of *Mycobacterium avium* complex (MAC) and 2 patient specimens of *Mycobacterium tuberculosis* (MTB) amplified by uniplex, duplex and multiplex PCR were hybridized with MTB and MAC probe, then assayed by Luminex Data are shown as FIGS. 1~3.

PCR products by uniplex PCR reaction were hybridized with MTB probe and MAC probe, then assayed by Luminex Result showed MTB probe only reacted with MTB specimen, but not with MAC specimen. MAC probe only reacted with MAC specimen, but not with MTB specimen (FIG. 1).

PCR products by duplex PCR reaction were hybridized with MTB probe and MAC probe, then assayed by Luminex Result showed MTB probe only reacted with MTB specimen, but not with MAC specimen. MAC probe only reacted with MAC specimen, but not with MTB specimen (FIG. 2).

PCR product by multiplex PCR reaction hybridized with MTB probe and MAC probe, then assayed by Luminex Result showed MTB probe only reacted with MTB specimen, but not with MAC specimen. MAC probe only reacted with MAC specimen, but not with MTB specimen (FIG. 3).

Figure 4:
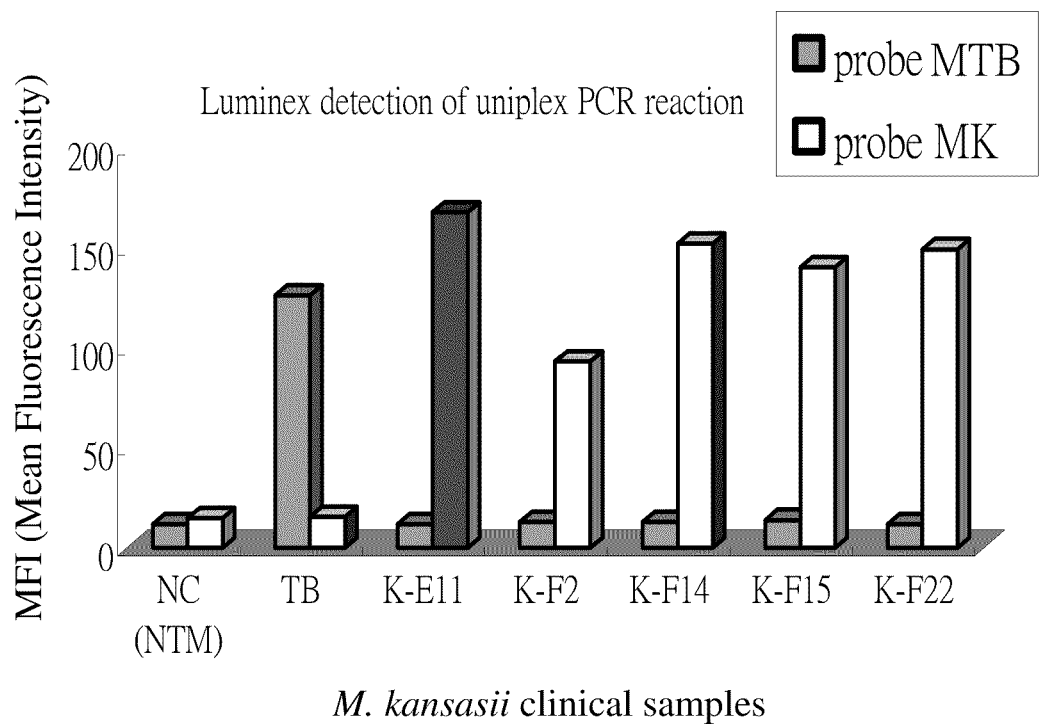
FIG. 4 illustrates the result of a PCR product by uniplex PCR reaction hybridized with MTB probe and MK probe, then assayed by Luminex TB represents a specimen from a tuberculosis patient. K-E11, K-F2, K-F14, K-F15 and K-F22 represent specimens from *Mycobacterium kansasii* patients. NC (NTM) represents the negative control (Nontuberculous mycobacteria).
Figure 5:
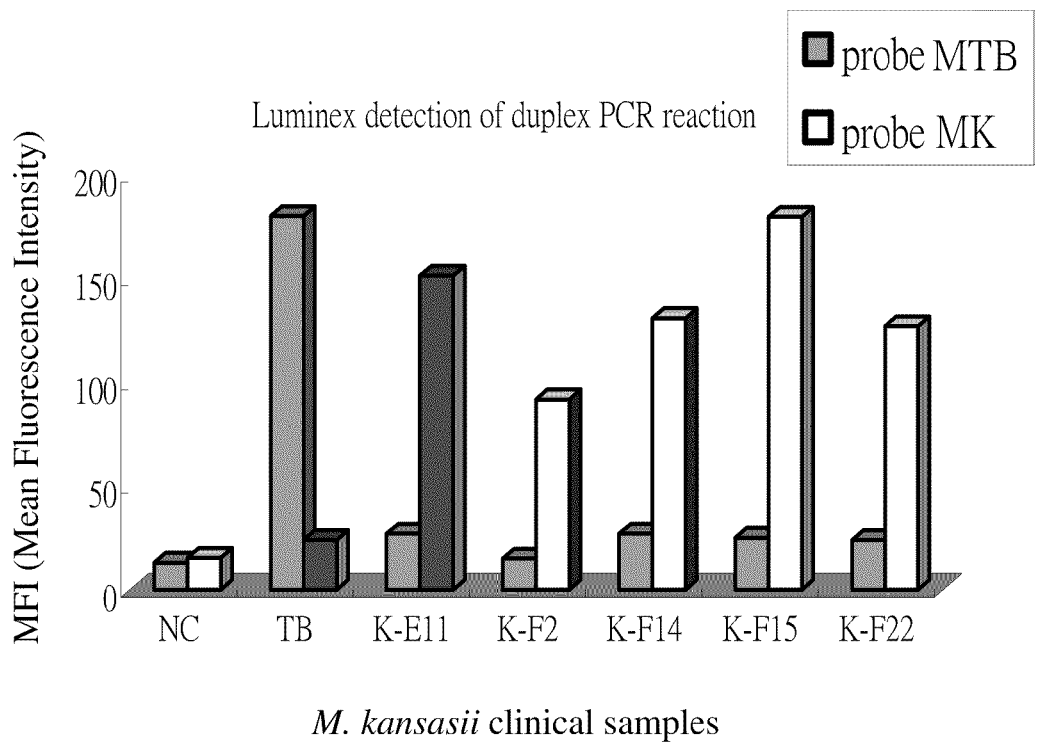
FIG. 5 illustrates the result of PCR products by duplex PCR reaction hybridized with MTB probe and MK probe, then assayed by Luminex TB represents a specimen from a tuberculosis patient. K-E11, K-F2, K-F14, K-F15 and K-F22 represent specimens from *Mycobacterium kansasii* patients. NC represents the negative control.
Figure 6:
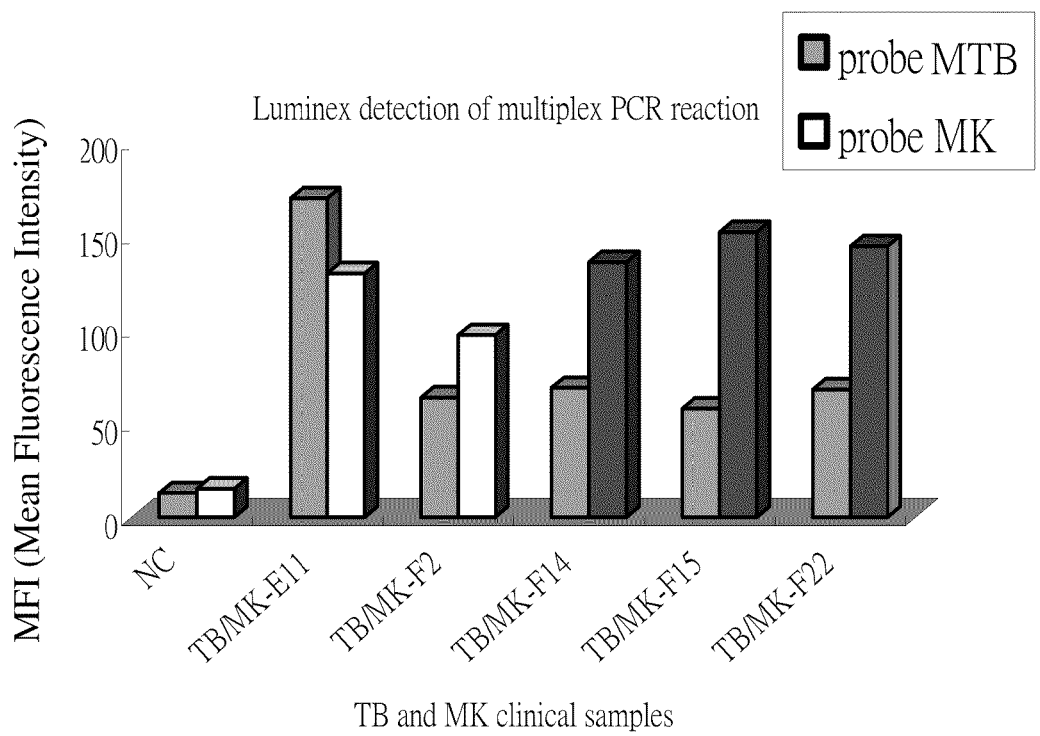
FIG. 6 illustrates the result of PCR products by multiplex PCR reaction hybridized with MTB probe and MK probe, then assayed by Luminex TB represents a specimen from a tuberculosis patient. K-E11, K-F2, K-F14, K-F15 and K-F22 represent specimens from *Mycobacterium kansasii* patients. "TB/MK" represents specimens containing a specimen from the tuberculosis patient and a specimen from one of the *Mycobacterium kansasii* patients. NC represents the negative control.

2. 10 patient specimens of *Mycobacterium kansasii* (MK) and 2 patient specimens of *Mycobacterium tuberculosis* (MTB) amplified by uniplex, duplex and multiplex PCR were hybridized with MTB and MK probe, then assayed by Luminex Data are shown as FIGS. 4~6.

PCR product by uniplex PCR reaction hybridized with MTB probe and MK probe, then assayed by Luminex Result showed MTB probe only reacted with MTB specimen, but not with MK specimen. MK probe only reacted with MK specimen, but not with MTB specimen (FIG. 4).

PCR product by duplex PCR reaction hybridized with MTB probe and MK probe, then assayed by Luminex Result showed MTB probe only reacted with MTB specimen, but not with MK specimen. MK probe only reacted with MK specimen, but not with MTB specimen (FIG. 5).

PCR product by multiplex PCR reaction hybridized with MTB probe and MK probe, then assayed by Luminex Result showed MTB probe only reacted with MTB specimen, but not with MK specimen. MK probe only reacted with MK specimen, but not with MTB specimen (FIG. 6).

Figure 7:
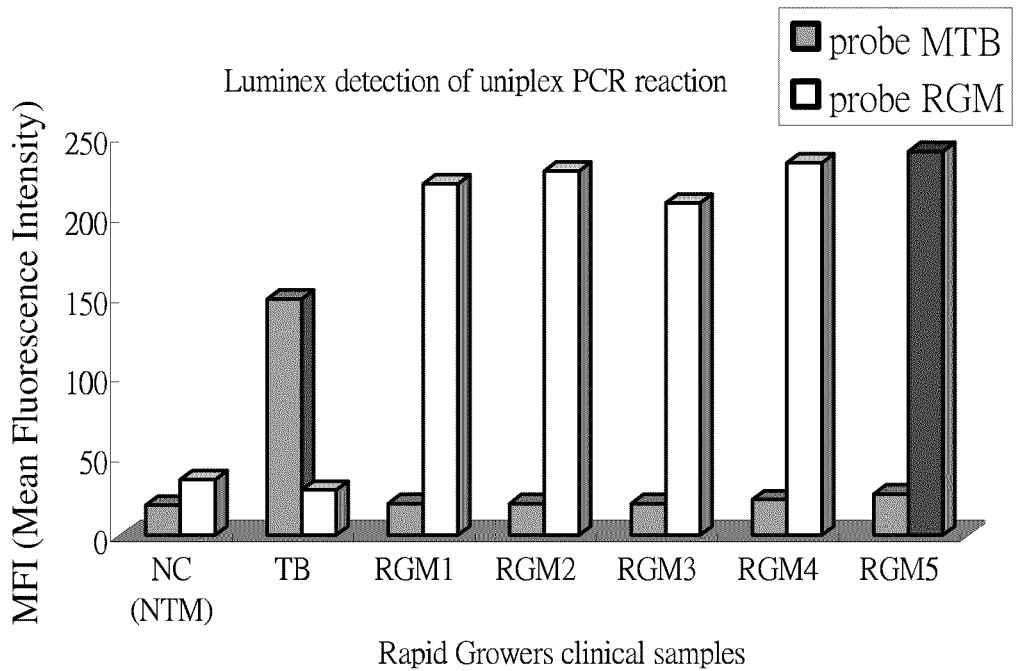
FIG. 7 illustrates the result of a PCR product by uniplex PCR reaction hybridized with MTB probe and RGM probe, then assayed by Luminex TB represents a specimen from a tuberculosis patient. RGM1, RGM2, RGM3, RGM4 and RGM5 represent specimens from Rapidly growing mycobacteria patients. NC (NTM) represents the negative control (Nontuberculous mycobacteria).
Figure 8:
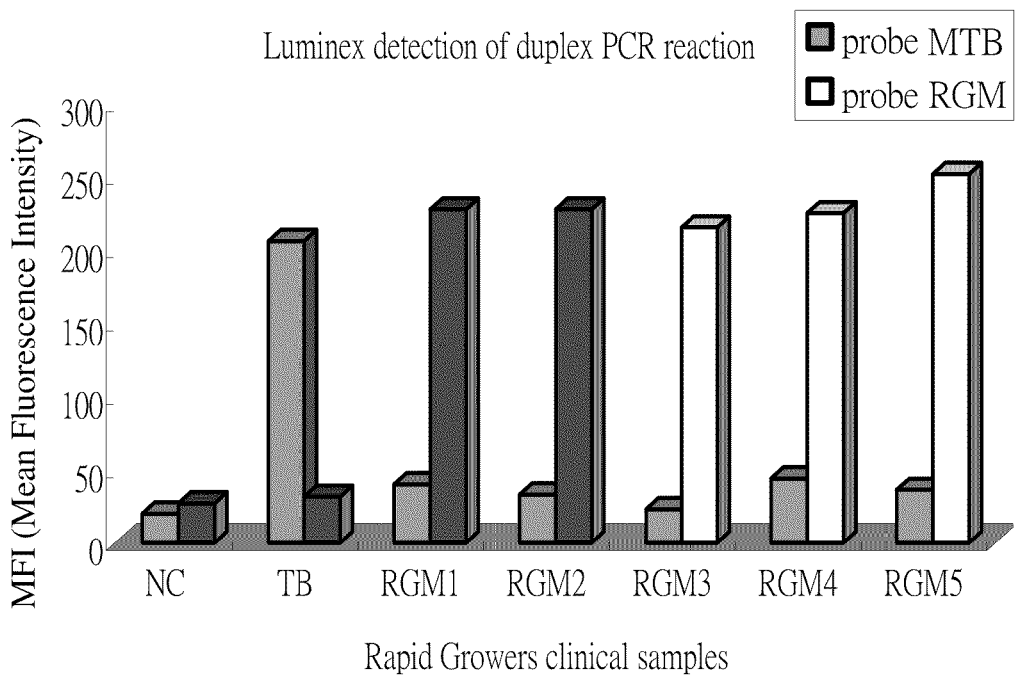
FIG. 8 illustrates the result of PCR products by duplex PCR reaction hybridized with MTB probe and RGM probe, then assayed by Luminex TB represents a specimen from a tuberculosis patient. RGM1, RGM2, RGM3, RGM4 and RGM5 represent specimens from Rapidly growing mycobacteria patients. NC represents the negative control.
Figure 9:
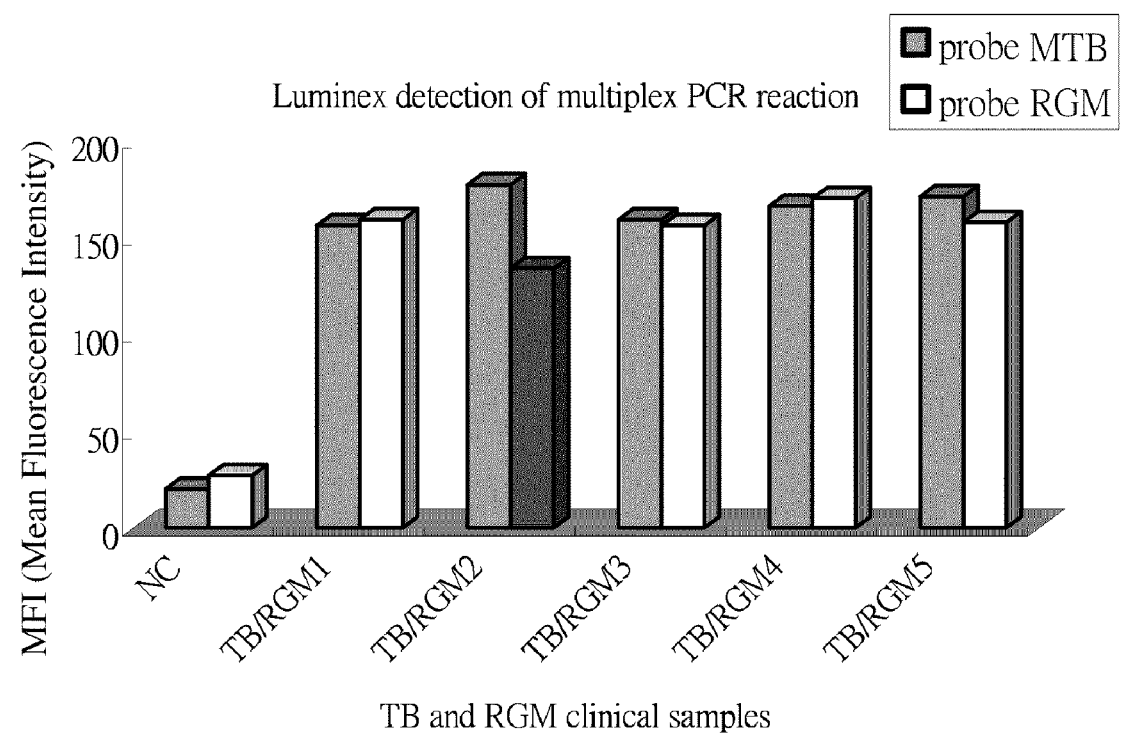
FIG. 9 illustrates the result of PCR products by multiplex PCR reaction hybridized with MTB probe and RGM probe, then assayed by Luminex TB represents a specimen from a tuberculosis patient. RGM1, RGM2, RGM3, RGM4 and RGM5 represent specimens from Rapidly growing mycobacteria patients. "TB/RGM" represents specimens containing a specimen from the tuberculosis patient and a specimen from one of the Rapidly growing mycobacteria patients. NC represents the negative control.

3. 10 patient specimens of Rapidly growing mycobacteria (RGM) and 2 patient specimens of Mycobacterium tuberculosis (MTB) amplified by uniplex, duplex and multiplex PCR were hybridized with MTB and RGM probe, then assayed by Luminex Data are shown as FIGS. 7~9.

PCR product by uniplex PCR reaction hybridized with MTB probe and RGM probe, then assayed by Luminex Result showed MTB probe only reacted with MTB specimen, but not with RGM specimen. RGM probe only reacted with RGM specimen, but not with MTB specimen (FIG. 7).

PCR product by duplex PCR reaction hybridized with MTB probe and RGM probe, then assayed by Luminex Result showed MTB probe only reacted with MTB specimen, but not with RGM specimen. RGM probe only reacted with RGM specimen, but not with MTB specimen (FIG. 8).

PCR product by multiplex PCR reaction hybridized with MTB probe and RGM probe, then assayed by Luminex Result showed MTB probe only reacted with MTB specimen, but not with RGM specimen. RGM probe only reacted with RGM specimen, but not with MTB specimen (FIG. 9).

What is claimed is:

1. A kit for differentiating *Mycobacterium tuberculosis* and Nontuberculous mycobacteria in a sample of tuberculosis comprising:
   (a) a primer pair for *Mycobacterium tuberculosis*,
   (b) a primer pair for Nontuberculous mycobacteria,
   (c) a probe for *Mycobacterium tuberculosis*, wherein the probe is SEQ. ID. NO. 5,
   (d) a probe for *Mycobacterium avium* complex, wherein the probe is SEQ. ID. NO. 6,
   (e) a probe for *Mycobacterium kansasii*, wherein the probe is SEQ. ID. NO. 7, and
   (f) a probe for Rapidly growing mycobacteria, wherein the probe is SEQ. ID. NO. 8.

2. The kit of claim 1, wherein the primer pair of (a) are SEQ. ID. NO. 1 and SEQ. ID. NO. 2.

3. The kit of claim 1, wherein the primer pair of (b) are SEQ. ID. NO. 3 and SEQ. ID. NO. 4.

4. The kit of claim 1, wherein each primer pair contains a recognizing particle labeled on a sense primer.

5. The kit of claim 4, wherein the recognizing particle is biotin.

* * * * *

SEQUENCE LISTING

```
<160> NUMBER OF SEQ ID NOS: 8

<210> SEQ ID NO 1
<211> LENGTH: 24
<212> TYPE: DNA
<213> ORGANISM: Mycobacterium tuberculosis
<221> NAME/KEY: primer_bind
<222> LOCATION: (1)..(24)

<400> SEQUENCE: 1
cgtacggtcg gcgagctgat ccaa                                              24

<210> SEQ ID NO 2
<211> LENGTH: 25
<212> TYPE: DNA
<213> ORGANISM: Mycobacterium tuberculosis
<220> FEATURE:
<221> NAME/KEY: primer_bind
<222> LOCATION: (1)..(25)

<400> SEQUENCE: 2
ttgacccaca agcgccgact gtcgg                                             25

<210> SEQ ID NO 3
<211> LENGTH: 25
<212> TYPE: DNA
<213> ORGANISM: Nontuberculous mycobacterium
<221> NAME/KEY: primer_bind
<222> LOCATION: (1)..(25)

<400> SEQUENCE: 3
ggagcggatg accacccagg acgtc                                             25

<210> SEQ ID NO 4
<211> LENGTH: 25
<212> TYPE: DNA
<213> ORGANISM: Nontuberculous mycobacterium
```

```
<221> NAME/KEY: primer_bind
<222> LOCATION: (1)..(25)

<400> SEQUENCE: 4
cagcgggttg ttctggtcca tgaac                                       25

<210> SEQ ID NO 5
<211> LENGTH: 17
<212> TYPE: DNA
<213> ORGANISM: Mycobacterium tuberculosis
<221> NAME/KEY: misc_binding
<222> LOCATION: (1)..(17)

<400> SEQUENCE: 5
caaaaccaga tccgggt                                                17

<210> SEQ ID NO 6
<211> LENGTH: 20
<212> TYPE: DNA
<213> ORGANISM: Mycobacterium avium
<221> NAME/KEY: misc_binding
<222> LOCATION: (1)..(20)

<400> SEQUENCE: 6
gccatcacgc cgcagaccct                                             20

<210> SEQ ID NO 7
<211> LENGTH: 21
<212> TYPE: DNA
<213> ORGANISM: Mycobacterium kansasii
<221> NAME/KEY: misc_binding
<222> LOCATION: (1)..(21)

<400> SEQUENCE: 7
atccgcccgg tggtcgccgc c                                           21

<210> SEQ ID NO 8
<211> LENGTH: 21
<212> TYPE: DNA
<213> ORGANISM: mycobacteria
<221> NAME/KEY: misc_binding
<222> LOCATION: (1)..(21)

<400> SEQUENCE: 8
tcggaaccag ccagctgtcg c                                           21
```